United States Patent [19]
Baron

[11] Patent Number: 5,867,250
[45] Date of Patent: Feb. 2, 1999

[54] APPARATUS AND METHOD FOR OPTICALLY MAPPING FRONT AND BACK SURFACE TOPOGRAPHIES OF AN OBJECT

[76] Inventor: William S. Baron, 330 Willow Rd., Menlo Park, Calif. 94025

[21] Appl. No.: 642,514

[22] Filed: May 3, 1996

[51] Int. Cl.$^6$ ........................................................ A61B 3/10
[52] U.S. Cl. .......................... 351/212; 351/211; 351/247; 356/395
[58] Field of Search ..................................... 351/205, 211, 351/212, 247; 356/395, 396; 359/618

[56] References Cited

U.S. PATENT DOCUMENTS

| | | | |
|---|---|---|---|
| 3,871,764 | 3/1975 | Nishizawa | 355/18 |
| 4,019,813 | 4/1977 | Cornsweet et al. | 351/14 |
| 4,761,071 | 8/1988 | Baron | 351/212 |
| 4,995,716 | 2/1991 | Warnicki et al. | 351/212 |
| 5,159,361 | 10/1992 | Cambier et al. | 351/212 |
| 5,406,342 | 4/1995 | Jongsma | 351/212 |
| 5,607,821 | 3/1997 | Haruki et al. | 359/618 |

*Primary Examiner*—Huy Mai
*Attorney, Agent, or Firm*—Flehr Hohbach Test Albritton & Herbert LLP

[57] ABSTRACT

Apparatus for determining the topography of a surface of an ophthalmic object comprising a projection branch for projecting along a first optical axis a projected structured light pattern onto the surface of the ophthalmic object. The projected structured light pattern has light and dark regions that form an array comprised of horizontal features and non-horizontal edges, an algorithm in the computer establishes at least one projected virtual point for the projected structured light pattern by fitting a first function to a non-horizontal edge and fitting a second function to a horizontal feature to establish an intersection and the coordinates of the projected virtual point. An imaging branch provides a pattern image of the projected structured light pattern along a second optical axis angled with respect to the first optical axis of the projected structured light pattern. The algorithm in the computer establishes at least one image virtual point for the image pattern by fitting a first function to a non-horizontal edge and fitting a second function to a horizontal feature to establish an intersection and the coordinates of the image virtual point. The algorithm in the computer determines the elevation at one location on the surface of the ophthalmic object from the coordinates of the image virtual point and determines the elevations at additional locations on the surface of the ophthalmic object in the same manner as the elevation at said one location for ascertaining the topography of at least a portion of the surface of the ophthalmic object.

31 Claims, 5 Drawing Sheets

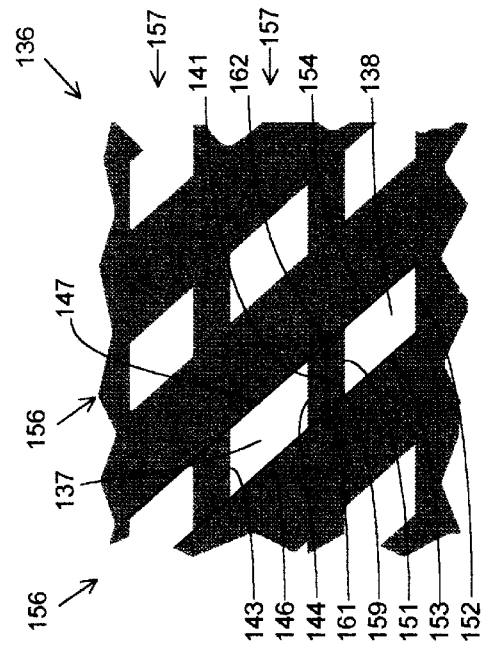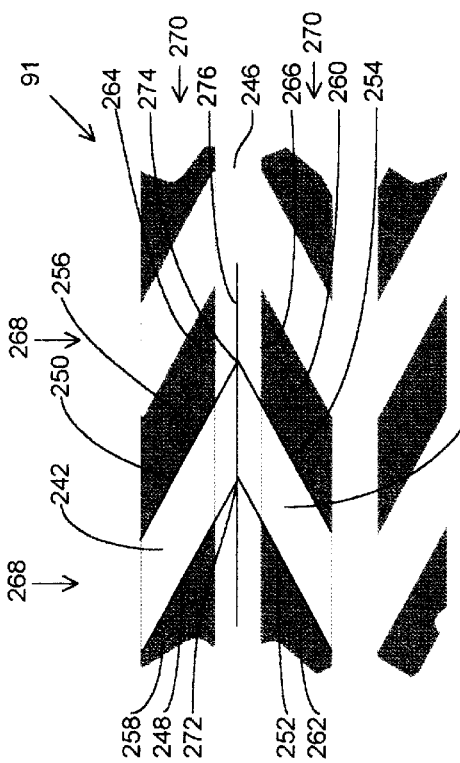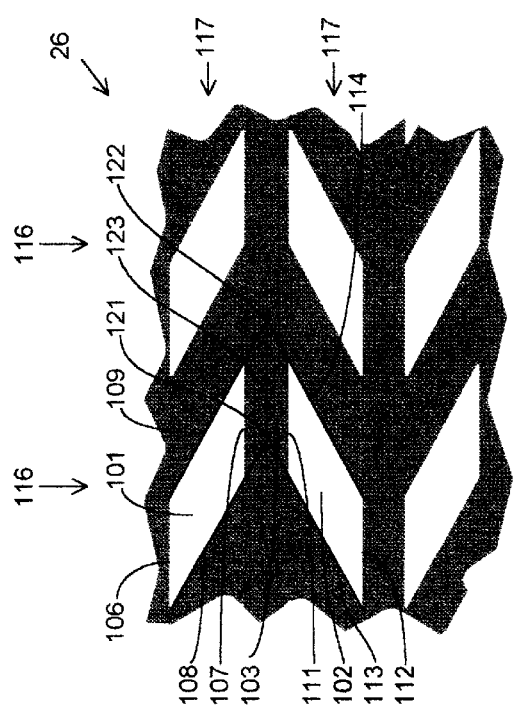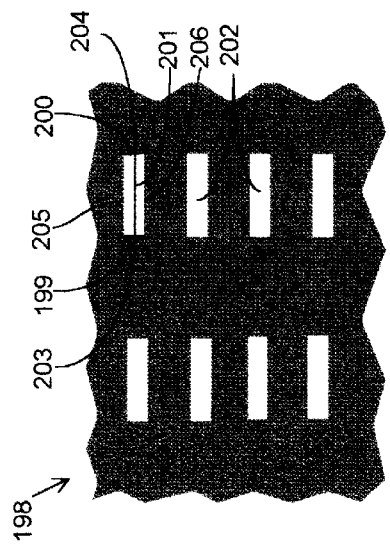

APPARATUS AND METHOD FOR OPTICALLY MAPPING FRONT AND BACK SURFACE TOPOGRAPHIES OF AN OBJECT

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

FIELD OF THE INVENTION

This invention relates to an apparatus and method for determining the front surface topography of objects that are transparent, translucent, or opaque, the back surface topography of objects that are transparent or translucent and the thickness of objects that are transparent or translucent. More particularly this invention relates to ophthalmic objects such as the eye's cornea.

BACKGROUND OF THE INVENTION

Videokeratoscopes heretofore obtained relative curvature readings from the cornea. They recorded specular reflections from the partially reflecting corneal surface and sought to model the surface by treating it as a convex mirror.

Typically videokeratoscopes illuminate the eye with a set of concentric rings and attempt to recreate the surface from the relative sizes of the rings as reflected from the cornea. The ring sizes have been used to document the relative surface curvature. However, attempts to reconstruct the three dimensional coordinates of the surface have had to make a priori assumptions about the cornea's shape. Since the shape of any particular person's cornea does not necessarily match the a priori assumed shape upon which the reconstruction calculation is based, the resulting topographic map can be erroneous. Also, there is an inability to measure the peripheral cornea, since ring mires projected and imaged from in front of the eye are obscured by facial features, which limit the extent of the image obtained from the periphery of the cornea. There is reduced accuracy in the central cornea because of both the absence of a central data point and because the absolute size of the ring mires within the central 3 mm are small. Sufficiently irregular corneas cannot be measured, because irregular corneal surfaces produce distorted images that cause neighboring rings to merge with each other, thus preempting image quantification.

Machine vision systems have been used to map a uniform and diffusely reflecting surface of an object. Structure was provided within an image of the surface by projecting a calibrated structured light pattern onto a front surface and obtaining an image of the projected pattern from a direction different than that of the projector. Computer algorithms are used to extract features from the projected light pattern and calculate the elevation of the surface from the elevation dependent displacements of the extracted features. However, structured light machine vision systems designed to map opaque objects may be inaccurate when used on translucent objects, due to alterations within the imaged pattern caused by light being imaged that arises from beneath the front surface.

Structured light topographic mapping systems have employed a fluorescent substance to map the corneal surface. These systems have assumed that the layer of fluorescing material, i.e. the tear film, is thin and that the substrate of the cornea, i.e. the corneal stroma, is not fluorescing. However, these assumptions do not necessarily hold in practice. The tear film varies in thickness, e.g. the tears pool at the lid margins and fill small irregularities in the corneal surface. In addition, the corneal stroma absorbs sodium fluorescein whenever the corneal epithelium is compromised such as following injury, in disease states, and during eye surgery.

Structured light topographic mapping systems employing a fluorescent substance have not addressed the alterations in an image caused by thick fluorescing tear films or a fluorescing corneal stroma.

Thus, there remains a need for an apparatus and method that can accurately measure the three dimensional coordinates of the corneal surface in the presence of tear film pooling and/or stromal fluorescence. In addition, there remains a need for an apparatus and method that can measure the thickness of the cornea over the entire extent of the cornea, and match the thickness profile of the entire cornea with the surface topography of the cornea.

SUMMARY OF THE INVENTION AND OBJECTS

In general it is an object of the present invention to provide an apparatus and method for optically mapping a surface of an object in which a structured light pattern having non-horizontal edges is utilized to provide virtual (reference) points for determining the topography of the surface.

Another object of the invention is to provide an apparatus and method of the above character which can be utilized for determining the topography of the front surface of objects that are transparent, translucent or opaque, the back surface topography of objects that are transparent or translucent and the thickness of objects that are transparent or translucent.

Another object of the invention is to provide an apparatus and method of the above character which can accurately measure the three dimensional coordinates of the corneal surface in the presence of tear film pooling and/or stromal fluorescence.

Another object of the invention is to provide an apparatus and method that can measure the thickness of the cornea over the entire extent of the cornea and match the thickness profile of the entire cornea with the surface topography of the cornea.

Another object of the invention is to provide an apparatus and method of the above character in which functions are fitted to two paired non-horizontal edges to establish an intersection and the coordinates of a virtual point utilized to determine the topography of a surface of an object.

Another object of the invention is to provide an apparatus and method of the above character in which a function is fitted to a non-horizontal edge and to a horizontal feature to establish an intersection and the coordinates of a virtual point utilized to determine the topography of a surface of an object.

Another object of the invention is to provide an apparatus and method of the above character in which imaged non-horizontal edges are equated to the front and back surfaces of an object and the corresponding coordinates of virtual points utilized to determine the topography of the front surface and back surface of the object.

Another object of the invention is to provide an apparatus and method of the above character in which the topography of the front surface is utilized to convert the apparent topography of the back surface to a true topography and the true topographies of the front and back surfaces are used to determine the thickness of the object at each of the virtual points.

Another object of the invention is to provide an apparatus and method of the above character which will maintain accuracy in the presence of optical blurring.

Another object of the invention is to provide an apparatus and method of the above character which can accommodate light within the image pattern that arises from regions posterior to the front surface due to substrate and/or thick tear film translucence.

Another object of the invention is to provide a projection apparatus for projecting a structured light pattern along an optical axis onto an object that has depth along the optical axis of the projector such that the pattern is in focus over the full extent of the object.

Additional objects and features of the invention will appear from the following description in which the preferred embodiments are set forth in detail in conjunction with the accompanying drawings.

BRIEF DESCRIPTION OF THE DRAWINGS

FIG. 4 is an enlarged view showing a central portion encircled by the line 4—4 of the projected structured light pattern shown in FIG. 2.

FIG. 5 is an enlarged view showing a portion of another embodiment of a projected structured light pattern incorporating the present invention.

FIG. 6 is an enlarged view showing a portion of still another embodiment of a projected structured light pattern incorporating the present invention.

FIG. 7 is an enlarged view showing a central portion encircled by the line 7—7 of the projected structured light pattern shown in FIG. 3.

DETAILED DESCRIPTION OF EMBODIMENTS

In general the apparatus for determining the topography of a surface of an ophthalmic object comprises means for projecting along a first optical axis a projected structured light pattern onto the surface of the ophthalmic object. The projected structured light pattern has light and dark regions that form an array comprised of non-horizontal edges and horizontal features. Means is provided for establishing at least one projected virtual point for the projected structured light pattern by fitting a first function to a non-horizontal edge and fitting a second function to a horizontal feature to establish an intersection and the coordinates of the projected virtual point. Means is provided which forms a pattern image of the projected structured light pattern along a second optical axis angled with respect to the first optical axis of the projected structured light pattern. Means is also provided for establishing at least one image virtual point for the image pattern by fitting a first function to a non-horizontal edge and fitting a second function to a horizontal feature to establish an intersection and the coordinates of the image virtual point. Means is provided for determining the elevation at one location on the surface of the ophthalmic object from the coordinates of the image virtual point. Means is also provided for determining the elevations at additional locations on the surface of the ophthalmic object in the same manner as the elevation at said one location for ascertaining the topography of at least a portion of the surface of the ophthalmic object.

Figure 1:
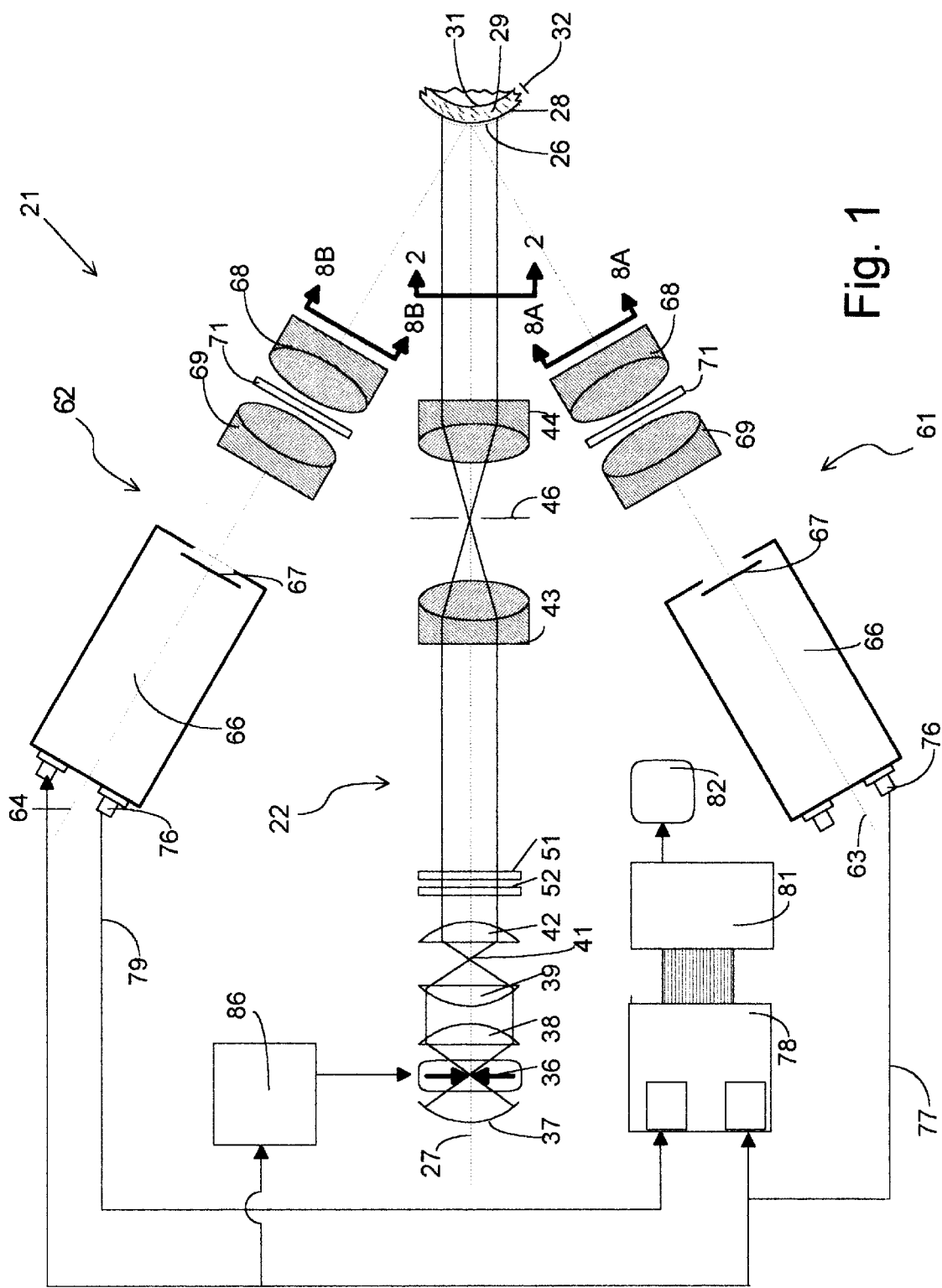
FIG. 1 is a schematic illustration of an apparatus for optically mapping a surface of an object incorporating the present invention.

More in particular, an optical apparatus 21 for optically mapping the surface of an object in accordance with the present invention is shown in FIG. 1. It consists of a projection branch 22 for projecting a structured light pattern 26 along a first optical axis 27 onto a first or front surface 28 of an ophthalmic object 29 such as a human cornea. The human cornea has a back or second surface 31 and a thickness 32 measured from the front surface 28 to the back surface 31.

The projection branch 22 includes a light source, 36, which for moving objects is preferably a stroboscopic source such as a Xenon flash lamp. A spherical mirror 37 increases the efficiency and directs the light through aspheric collimating lens 38 and aspheric condensing lens 39 to a focus conjugate 41 with a shorter focal length collimating lens 42. The light source 36 is conjugate with the first focal plane of the collimating lens 42 and is conjugate with a second focal plane of lens 43 and a first focal plane of lens 44. An optical aperture 46 is placed in a plane that is conjugate with the light source 36. As for example as shown in FIG. 1, optical aperture 46 is placed between lenses 43 and 44. Alternatively, it can be placed between lenses 39 and 42.

A reticule 51, which provides the structured light pattern 26, is approximately conjugate with the ophthalmic object 29. The reticule 51 is positioned beyond the collimating lens 42 so that light passing through it is collimated. Since the light passing from the exit lens 44 is also collimated, there is little or no magnification change in the structured light pattern 26 over the usable depth of field. Thus, an advantage of the present projection system is that the x,y coordinates of the imaged reticule are constant throughout the usable depth of field of the projected reticule.

A preferred configuration of the projection branch 22 is when the spacing between imaging lenses 43 and 44 is equal to the sum of the focal lengths of said lenses. Thus configured, the bundles of light comprising the image of the reticule at the object are essentially parallel to the optical axis 27, and displacement of the image detail does not occur as a function of the distance along the optical axis 27. Accordingly, this provides for simplicity in the calibration of the apparatus, as the coordinates of the projected virtual points can be treated as being invariant.

Furthermore, the aforementioned configuration of the projection branch facilitates the use of a thick reticule of the type hereinafter described in order to increase the effective depth of field without reducing the size of the aperture. The projection branch's source is collimated at the reticule, 51, as well as at the object, 29, thus the reticule can be designed such that it has substantial thickness along the optical axis, 27.

A fluorescein excitation filter 52 can be provided in the projection branch 22. The fluorescein excitation filter 52 is utilized when the ophthalmic object 29 is treated with a fluorescent substance. As is well known to those skilled in the art, the optimal wavelengths of the light transmitted by the fluorescein excitation filter 52 is dependent on the fluorescent excitation and emission spectra of the fluorescent material. For ophthalmic solutions of sodium fluorescein, the optimal excitation wavelengths are between 460 and 510 nm, and the emission wavelengths are between 520 and 560 nm.

The optical apparatus 21 also includes at least one imaging branch. As shown in FIG. 1 the apparatus is provided with first and second imaging branches 61 and 62 with the first imaging branch 61 being disposed along a second optical axis 63 and the second imaging branch 62 being disposed along a third optical axis 64 both of which are angularly offset with respect to the first optical axis by suitable angles such as 15°–60° and preferably approximately 30°. The second and third optical axes 63 and 64 intersect the first optical axis in proximity to the surface 28 of the ophthalmic object 29. Each of the first and second imaging branches 61 and 62 include a video camera 66 which is provided with a detector 67. Each imaging branch secures an image of the projected structured light pattern, i.e. a pattern image. The detector 67 is preferably a solid state imaging device consisting of an array of light detecting elements. The detector 67 is conjugate with at least a portion of the ophthalmic object 29. A pair of lenses 68 and 69 form an image, i.e. a pattern image, of the structured light pattern 26, which is projected onto the ophthalmic object 29, on the solid state detector 67. The camera 66 can be tilted relative to the optical axis of the lenses 68 and 69 in order to optimize use of the depth of focus of the imaging branch for a particular object. For example, a flat object positioned orthogonal to the projection branch could be optimally imaged by tilting the camera such that the detector is parallel to the flat object. A fluorescein emission filter 71 is provided in each of the first and second imaging branches 61 and 62. This filter 71 blocks the excitation wavelengths and optimally passes the emission spectrum of the fluorescent material applied to the ophthalmic object 29.

Each of the video cameras 66 is provided with an output terminal 76 on which there is provided a composite video signal. The first imaging branch 61 is connected by a conductor 77 to an input of a video capture device in the form of a frame grabber 78. The second imaging branch 62 is connected by another conductor 79 to the frame grabber 78 as shown in FIG. 1. The output of the frame grabber 78 is supplied to a general purpose computer 81 which is provided with an output monitor 82. When there are at least two imaging branches, as for example imaging branches 61 and 62 as shown in FIG. 1, one of the cameras can be utilized to synchronize the other camera(s) and the frame grabber. Alternatively, synchronization signals from a common source (not shown) can be utilized for driving all the cameras in the imaging branches as well as the frame grabber. Preferably, a single frame grabber as shown having simultaneous inputs is used, although multiple image capture boards can be utilized. Simultaneous frame grabbing can be accomplished by using a color RGB frame grabber, i.e. a frame grabber in which each of the three color channels is stored in an independent and parallel memory plane, that is synchronized to the common source or the master camera. With an RGB frame grabber, the output of each monochrome camera is input into a separate color plane, and treated as a distinct monochromatic image. Each image is represented as an array of numbers, the value of each number being preferably a linear representation of the light intensity at a corresponding point in the optical image. Thus, each number in the array represents a pixel.

The synchronization signal utilized for synchronizing the cameras and frame grabber is utilized for synchronizing the operation of a trigger module 86 for operation of the stroboscopic light source 36 so that there is one flash from the light source for each video frame cycle.

The frame grabber 78 operates in a conventional manner and performs an analog-to-digital conversion on the video signal then stores the image in the computer memory of the computer 81. When digital cameras are used, analog-to-digital conversion is performed at the camera rather than at the frame grabber. The digital representation of the image is transferred from the frame grabber 78 to the general purpose computer 81 for processing. The live image, the frozen grabbed image, the results of the feature extraction process and topography and thickness data can be visualized on the video monitor 82. The computer 81 is provided with a standard keyboard (not shown) and pointing devices (not shown) to interface with the general purpose computer for controlling the optical apparatus 21.

Operation and use of the optical apparatus 21 in conjunction with the method of the present invention may now be described utilizing the projected structured light pattern 26 also of the present invention. As hereinbefore explained, the apparatus and method of the present invention is particularly useful in making measurements of ophthalmic objects as for example the human cornea that have a thickness and a non-opaque substrate. It should be appreciated that the apparatus and method of the present invention can also be utilized with other types of objects, as for example opaque objects on which the front surface can be mapped. The apparatus and method of the present invention can be utilized for accurately measuring three-dimensional coordinates of the corneal surface in the presence of tear film pooling and/or stromal fluorescence. Front and back surface topographic measurements can be made. Thickness of the cornea can be measured over the entire extent of the cornea making it possible to match the thickness profile of the entire cornea with the surface topography of the cornea.

These capabilities are made possible by the use of the structured light pattern 26 (see FIGS. 1, 2, and 4) incorporated in the present invention. With respect to the structured light pattern, the term horizontal refers to the orientation that is orthogonal to the optical axis 27 of the projection branch and parallel to the plane formed by the intersection of the first optical axis 27 of the projection branch and the second optical axis 63 of the first imaging branch 61. The term vertical refers to the orientation that is both orthogonal to the first optical axis 27 of the projection branch 22, and orthogonal to the horizontal.

When the ophthalmic object 29 to be mapped, is a human cornea it can be characterized as having a translucent substrate; that is, the structure of the cornea partially reflects and partially transmits incident light. This structure can be made more translucent by the addition of chemical agents, including fluorescing agents. For example, the stroma of an eye with the epithelium removed is a translucent substrate both with and without the addition of sodium fluorescein, but it diffusely emits more light with sodium fluorescein than without sodium fluorescein when illuminated by fluorescent excitation wavelengths.

In connection with the present invention, the term thick film means a layer of material that acts as a translucent substrate and is thick in comparison to the desired accuracy of the topographic map. For example a pool of tears containing sodium fluorescein is considered to be a thick film. Conversely, the term thin film means a layer of material that is thin in comparison to the desired accuracy of the topographic measurements being made. Thin film, for example, can be the diffusing surface of an opaque substrate.

Figure 2:
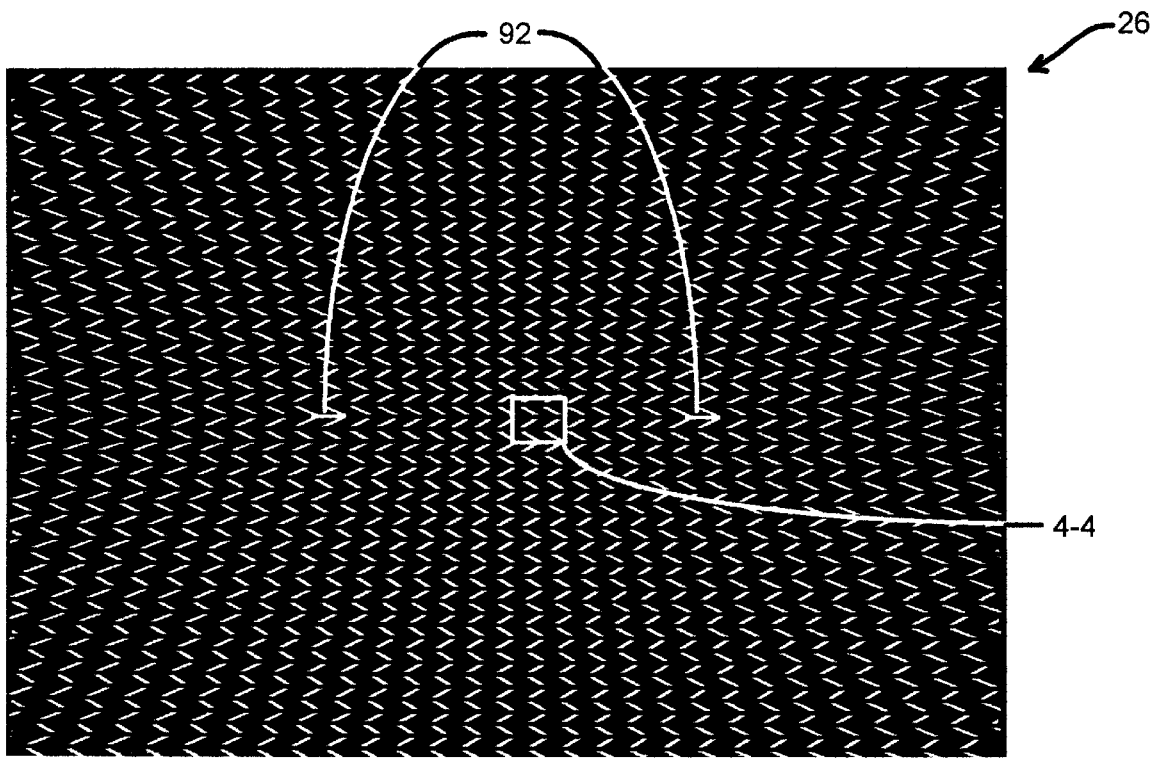
FIG. 2 is a computer generated pattern incorporating the present invention for producing a projected structured light pattern in the apparatus shown in FIG. 1.
Figure 3:
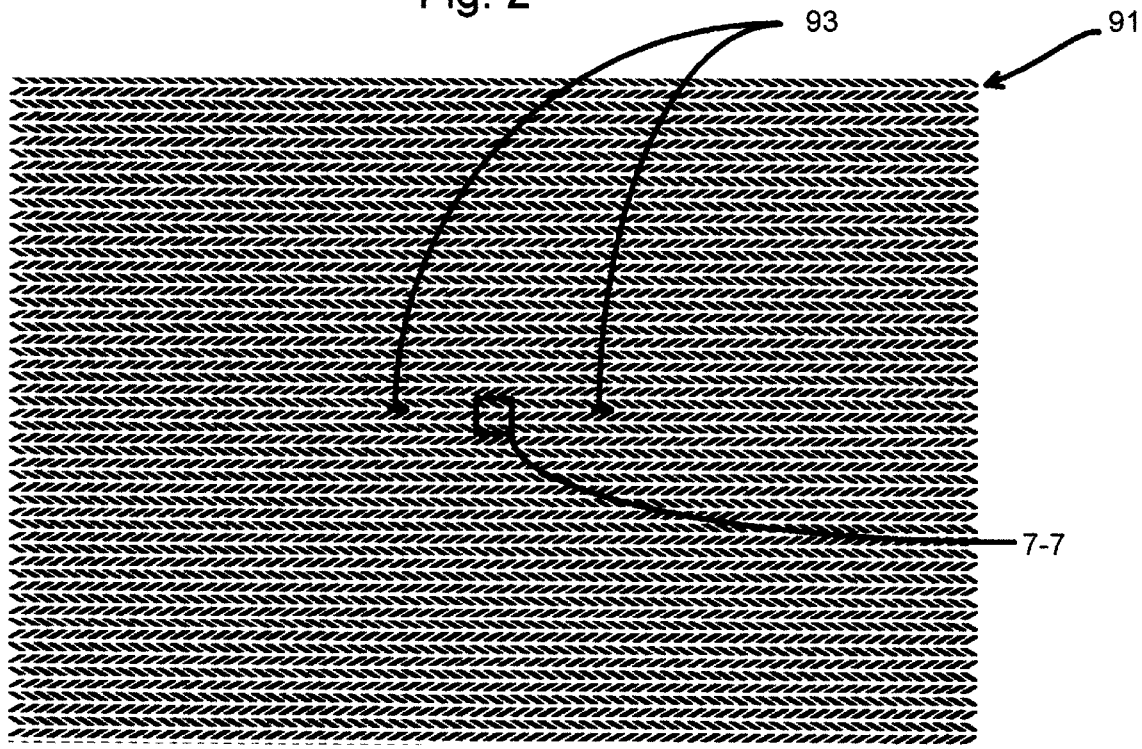
FIG. 3 is similar to FIG. 2 showing an alternative embodiment of a computer generated pattern.

A representative structured light pattern 26 of the type incorporating the present invention and in the apparatus of FIG. 1 is shown in FIG. 2. Another representative light pattern 91, which has inter-element spacing optimized for measuring a thin film is shown in FIG. 3. Fiducial marks 92 and 93 are provided respectively in the patterns 26 and 91 for orientation purposes when utilized in the apparatus of the present invention.

In FIG. 4 there is shown an enlarged portion, demarcated by region 4—4 in FIG. 2, of the projected light pattern 26. As shown the projected light pattern 26 is comprised of a plurality of vertically juxtaposed light regions 101 and 102 essentially in the form of pairs of quadrilaterals of the light regions 101 having horizontally disposed upper and lower edges 106 and 107 to provide horizontal features. They are also provided with left and right edges 108 and 109 which are inclined from the horizontal by a suitable angle such as 30 degrees to provide non-horizontal edges. Similarly, the light regions 102 are provided with upper and lower edges 111 and 112 that provide horizontal features and left and right edges 113 and 114 that provide non-horizontal edges. The left and right edges 113 and 114 are inclined to the horizontal in opposite direction to that of left and right edges 108 and 109 to form two pairs of vertically juxtaposed paired non-horizontal edges. The vertically and horizontally spaced apart light regions 101 and 102 are disposed generally in columns 116 with every other light region being offset in an opposite direction from the vertically adjacent light region. The light regions 101 and 102 also lie in horizontal rows 117.

The dark regions 103 between the vertically disposed apart light regions 101 and 102 can be characterized as gutters. Within each gutter there are two virtual points 121 and 122. The coordinates of the virtual points 121 and 122 are delineated by the intersection of two discontinuous and discrete functions which are mathematical extensions of the paired left edges 108 and 113 and paired right edges 109 and 114. As can be seen, the virtual points 121 and 122 optionally lie on the midline 123 of the region bounded by juxtaposed ends of regions 101 and 102. The midline 123 is a spaced apart horizontal feature.

A preferred function for defining the edge of a light region is a straight line as defined by Equation 1.

$$Y = a + bX \quad \text{Equation 1}$$

where Y is the dependent vertical variable, X is the independent horizontal variable, a is a constant and b is a constant. Preferably, the light regions 101 and 102 are dimensioned such that the virtual points defined by the simultaneous solutions of the juxtaposed discontinuous edge functions are midway between the juxtaposed ends of the bounding light regions. For straight line edge functions, the Y coordinate and X coordinate of a virtual point are defined by respectively by $$Y = \frac{b_2 a_1 - b_1 a_2}{b_2 - b_1} \quad \text{Equation 2}$$

$$X = \frac{Y - a_1}{b_1} \quad \text{Equation 3}$$

where $a_1$, $a_2$, $b_1$ and $b_2$ are constants from straight line functions fit to juxtaposed paired discontinuous edges. Additional virtual points are defined similarly throughout the structured light pattern 26 for all of the juxtaposed paired quadrilaterals.

Pattern 26 provides several advantages for defining virtual points. One advantage of pattern 26 is that the coordinates of the virtual points 121 and 122 are defined by both the intersection of the paired non-horizontal edge functions and the intersections of these functions with the horizontal midline of the gutter, a horizontal feature. These redundant means for finding the coordinates of the virtual points provides a means for checking on the accuracy of the method of the present invention. Another advantage of pattern 26 is that the horizontal edges, i.e. horizontal edges 106 and 107 for quadrilateral 101 and horizontal edges 111 and 112 for quadrilateral 102, can be used to define additional spaced apart horizontal features such as the midline between the two end edges of a given quadrilateral. This midline defines a horizontal feature that intersects the function fitted to a non-horizontal edge of the given quadrilateral. Utilizing the midline as a spaced apart horizontal feature provides additional virtual points with which to measure the surface. Moreover the coordinates of these virtual points are defined by different features than the virtual points defined by the intersection of paired non-horizontal functions.

A special case of the discontinuous bar edge pattern occurs when the gutter is reduced to zero. In this instance, the virtual points become real points. Preferably the gutter is finite because optical blur at the juncture of the light regions can distort the defining edge functions. With such a pattern, the vertical coordinate of the intersection point of the functions fit to the paired edges serves as a horizontal feature.

Thus the pattern 26 can be characterized as having light regions and dark regions which are sized and arranged so as to form an array of edges that is optimized to measure objects and substrates that are opaque, translucent or transparent; light pattern 26 has been optimized for measuring the human cornea when the stroma is characterized as being translucent. The horizontal separation between horizontally adjacent light quadrilaterals increases from the center of the pattern to the periphery, since the corneal thickness increases from the center to the periphery.

From the foregoing it can be seen and generally stated that the light and dark regions of a structured light pattern of this invention form an array of edges, at least certain of which are non-horizontal edges, and, optionally, horizontal edges or lines. The non-horizontal edges within the array of edges are used to find mathematical intersections that define the two-dimensional coordinates of points within the projected and imaged array of edges. Functions are fitted to the non-horizontal edges and either a paired intersecting non-horizontal edge function is utilized to define an intersection point or a paired intersecting horizontal feature is used to define an intersection point. A horizontal feature can be a horizontal edge or any reference point derived from or dependent upon a horizontal edge such as a spaced apart horizontal line, or a horizontal feature can be the vertical coordinate of an intersection point formed by the intersection of functions fit to two paired non-horizontal edges. The points defined by intersecting functions are theoretical points and can be located within uniform regions of the structured light pattern and are referred to as virtual points.

As hereinafter described, it will be made apparent that the use of non-horizontal edges to define the coordinates of a virtual point is central to the clinical advantages of the present invention. Selective use of the non-horizontal edges provides means for maintaining front surface measurement accuracy in the presence of light emissions posterior to the front surface, thus providing the eye care practitioner a means for accurately measuring the corneal shape of eyes that are prone to absorb fluorescein instilled in the tear layer, such as accidentally traumatized eyes, eyes undergoing surgical procedures, and diseased eyes. Moreover, corneas that are diffusing, as during corneal refractive surgery laser procedures, pose imaging conditions similar to eyes that absorb fluorescein and thus the selective use of the non-horizontal edges provides means for measuring the shape of the cornea intraoperatively without the use of a fluorescing agent. These attributes of the imaged pattern of the present invention are discussed hereinafter.

Another embodiment of the structured light pattern incorporated in the present invention is shown by the structured light pattern 136 in FIG. 5. The structured light pattern 136 consists of a plurality of vertically juxtaposed paired light regions 137 and 138 with horizontal dark gutters 141 interposed there between. Light region 137 is provided with a horizontal upper edge 143, and a horizontal lower edge 144, which provide horizontal features, and a left edge 146 and a right edge 147, which provide non-horizontal edges. Similarly, light region 138 is provided with a horizontal upper edge 151 and a horizontal lower edge 152, which provide horizontal features, and a left edge 153 and a right edge 154, which provide non-horizontal edges. The light regions 137 and 138 are disposed in angled columns 156 and horizontal rows 157. Left edges 146 and 153 form a pair and right edges 147 and 154 form another pair. Each of these pairs of edges is preferably defined by a continuous function. The non-horizontal edges of the light regions 137 and 138 may be defined by curvilinear functions. However, they still could be analyzed as essentially being quadrilaterals such that for a vertically juxtaposed pair of quadrilaterals a straight line function can be fit to a pair of edges wherein the intersection with the midline 159 of the gutters, a horizontal feature, defines virtual points 161 and 162. It can be seen that additional virtual points are defined similarly throughout the structured light pattern 136 for all of the paired juxtaposed quadrilaterals, the paired edges of which are connected by continuous functions. A pattern with vertically oriented quadrilaterals and non-horizontal edges is a special case of pattern 136. An advantage of the pattern 136 is that the non-horizontal edge function is interpolated, not extrapolated, at the point of intersection with the midline of the gutter, a horizontal feature.

The functions defining the non-horizontal edges of the light regions 137 and 138 are not restricted to any particular form. Curvilinear functions such as second degree polynomial equations are preferred for patterns consisting of continuous edges when the horizontal spacing between the quadrilaterals varies over the extent of the pattern in order to optimize the pattern for a translucent substrate or thick film that varies in thickness, e.g. the human cornea.

Another embodiment of the structured light pattern incorporating the present invention is shown in the structured light pattern 198 in FIG. 6. In pattern 198, the vertical height of the quadrilaterals is so small that the pattern may be characterized as an array of horizontal lines, 202, vertically and horizontally spaced apart. As in patterns 26 and 136, the sides 199 and 200 of the quadrilaterals are used to define non-horizontal edges and the horizontal end edges 205 and 206 are used to define horizontal features. The coordinates of the associated virtual points, 203 and 204, can be obtained from the intersection of the non-horizontal edges 199 and 200, and the midline 201, a horizontal feature, of the thin quadrilateral. The pattern 198 makes it possible to tightly pack the virtual points, thereby increasing the sampling density of the pattern.

Another embodiment of the structured light pattern incorporating the present invention is shown in the structured light pattern 91 in FIG. 7 which shows an enlarged region as demarcated by 7—7 in FIG. 3. The pattern 91 is provided with vertically juxtaposed light regions 242 and 244 that are essentially in the form of quadrilaterals that are contiguous with a separating light gutter 246. The quadrilaterals 242 and 244 having left and right edges 248 and 250 and 252 and 254, respectively, which are offset from the horizontal by a suitable angle such as 30 degrees. The left and right edges 248 and 250 are inclined from the horizontal in opposite direction to that of edges 252 and 254. The light quadrilaterals 242 and 244 are bounded by abutting dark regions 256 and 258 and 260 and 262, respectively. The dark regions form horizontal edges 264 and 266 with a light gutter 246 that provides horizontal features that can be used to define a midline, a spaced apart horizontal feature, for the light gutter. The light regions 242 and 244 are disposed generally in columns 268 with every other light region being offset in an opposite direction from the vertically adjacent light region. Similarly, the light regions 242 and 244 lie in horizontal rows 270.

Within each light gutter 246 there are two virtual points 272 and 274. The coordinates of virtual points 272 and 274 are defined by the intersection of two discontinuous and discrete functions which represent mathematical extensions of the paired left edges 248 and 252 and paired right edges 250 and 254. As can be seen, the virtual points 272 and 274 preferably lie on the midline 276 of the horizontal light gutter demarcated by the juxtaposed horizontal edges 264 and 266.

In accordance with the present invention, non-horizontal edges are grouped according to their relationship to a specified imaging branch of the apparatus shown in FIG. 1. The term contralateral edge means a non-horizontal edge formed by abutting light and dark regions in which the light region is on the same side of the edge as the designated imaging branch. The term ipsilateral edge means a non-horizontal edge formed by abutting light and dark regions in which the light region is on the opposite side of the edge from the designated imaging branch. The contralateral edges for imaging branch 61 as viewed in FIG. 8A—8A and the ipsilateral edges for imaging branch 62, as viewed in FIG. 8B—8B using pattern 26, correspond to edges 108 and 113, in pattern 136 correspond to edges 146 and 153, in pattern 198 correspond to edges 199, and in pattern 91 correspond to edges 248 and 252. The contralateral edges of imaging branch 62 as viewed in Figure view 8B—8B, and the ipsilateral edges for imaging branch 61 as viewed in FIG. 8A—8A, in pattern 26 correspond to edges 109 and 114, in pattern 136 correspond to edges 147 and 154, in pattern 198 correspond to edges 200, and in pattern 91 correspond to edges 250 and 254.

Figure 8B:
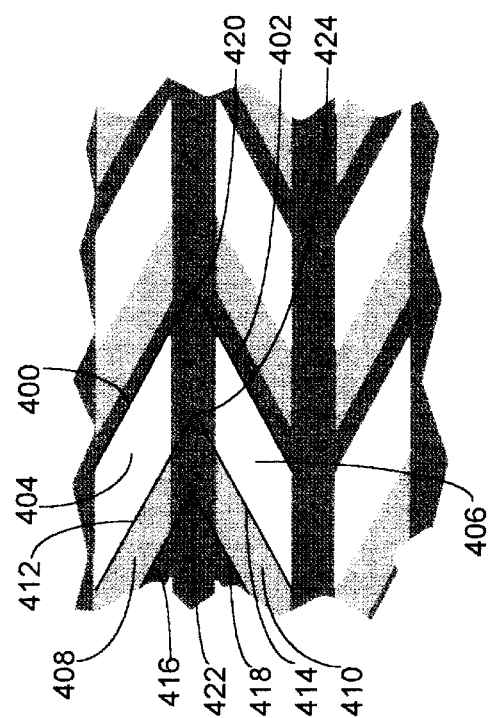
FIG. 8B is a view looking along the line 8B—8B of FIG. 1 showing a portion of the image obtained by the second imaging branch of the apparatus shown in FIG. 1 for a translucent substrate.
Figure 8A:
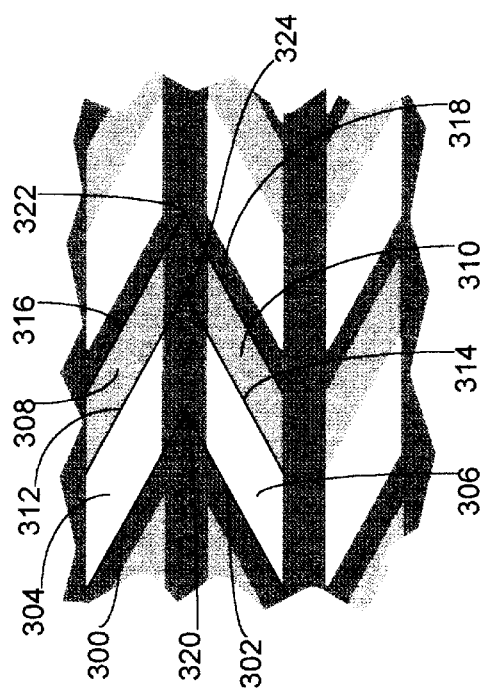
FIG. 8A is a view looking along the line 8A—8A of FIG. 1 showing a portion of the image obtained by the first imaging branch of the apparatus shown in FIG. 1 for a translucent substrate.

Operation and use of the apparatus and patterns of the present invention may now be briefly described as follows. When measuring a thick film or translucent substrate, the image pattern of a projected structured light pattern has secondary light regions contiguous with the primary light regions. The secondary light regions are formed by light coming from deep within the thick film or translucent substrate. The primary light regions are formed by light coming from the front surface. Accordingly, the secondary light regions are on the ipsilateral side of the imaged pattern. The relative intensity of the primary and secondary light regions is dependent on the translucency or fluorescence of the object. This image pattern phenomenon is referred to herein as smearing. Image patterns obtained using a projected light pattern 26 are shown diagramatically in FIGS. 8A and 8B for an object having a translucent substrate. FIG. 8A depicts the pattern image obtained from imaging branch 61 and FIG. 8B depicts the pattern image obtained from imaging branch 62 for a segment of pattern 26. In each image, there are contiguous secondary light regions 308 and 310 and 408 and 410, respectively, that are adjacent to the primary projected light regions 304 and 306 and 404 and 406, respectively. The contralateral edges are unaffected by the light originating behind the front surface, and functions fit to the paired contralateral edges 300 and 302 and 400 and 402, intersect to define the image coordinates of contralateral virtual points 320 and 420 respectively. Depending on the degree of translucency and the homogeneity of the substrate, a boundary may be identifiable between the primary light region and the secondary light region. Functions may be fit to these paired boundaries 312 and 314 and 412 and 414, respectively, to define the image coordinates of boundary virtual points 324 and 424, respectively. Boundary virtual points may be used to find front surface elevations, however, due to a reduced signal to noise ratio, the lower contrast edges used to define them are not necessarily as accurately defined in practice as the higher contrast contralateral edges. On the ipsilateral side of the secondary light regions there is an ipsilateral edge, the back surface ipsilateral edge, that is formed by light coming from the back surface of the substrate or thick film. The virtual point defined by a back surface ipsilateral edge is a back surface ipsilateral virtual point. Functions fit to paired back surface ipsilateral edges 316 and 318 and 416 and 418 can be used to define the coordinates of back surface ipsilateral virtual points 322 and 422, respectively. These back surface ipsilateral virtual points may be used to find the elevation of the back surface.

Analogous contiguous secondary light regions occur in the pattern image of alternative embodiments of the imaged structured light pattern, thereby forming associated back surface ipsilateral edges that define the coordinates of back surface ipsilateral virtual points. Likewise the position of the contralateral edges of alternative embodiments of the structured light pattern are unaffected by the nature of the substrate.

Operation and use of the apparatus in topographically mapping the front surface, the back surface and the thickness of an object, the human cornea, may now be briefly described. The elevation of the front surface may be calculated from the position of an imaged contralateral virtual point using the calibration data. For thin films, the ipsilateral virtual point data may be merged with the contralateral virtual point data. For thick films and translucent substrates, the contralateral virtual point data is used to reconstruct the front surface, so that the apparent back surface, as represented by the raw ipsilateral virtual point coordinates, can be converted to true spatial coordinates.

Figure 9:
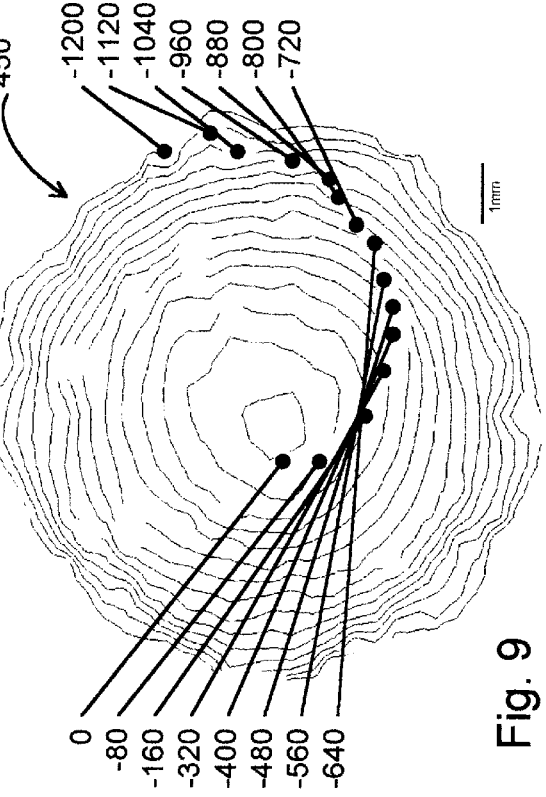
FIG. 9 is a contour plot (80$\mu$ intervals) of the front surface topography of an artificial cornea made from fluorescing plastic examined by the apparatus of FIG. 1.

A topographic contour map 450 of the front surface of an artificial cornea measured with the present invention is shown in FIG. 9. The artificial cornea, which is made from fluorescent plastic, is used to calibrate ophthalmic lasers and for personnel training. It is approximately as thick as the human cornea. The contour map in FIG. 9 of the front surface is obtained by projecting structured light pattern 26 along the optical axis 27 onto the surface of the artificial cornea. As previously described, projected pattern 26 provides an array of edges, some of which are non-horizontal edges. As part of the calibration procedure prior to use of the instrument, straight line functions are fit to pairs of non-horizontal edges within the projected array of edges. The intersections of the paired straight line functions in the projected array of edges are used to define the coordinates on the surface of the corresponding virtual points. Whereas this ophthalmic object has a translucent substrate and the front surface is being mapped, the contralateral edges within the pattern image are used to determine the front surface topography. Accordingly, straight line functions are fitted to paired contralateral edges within the pattern image obtained by each imaging branch. The simultaneous solution, i.e. the intersections, of the paired straight line functions within the pattern image are used to establish the coordinates of the corresponding contralateral virtual points. The vertical coordinate of the simultaneous solution acts as an intersecting horizontal feature, along with the midline of the gutter. The coordinates of the pattern image's contralateral virtual points are converted to elevation data. The conversion is accomplished by utilizing conversion functions based upon the optical geometry of the apparatus and stored in the computer. These conversion functions are readily ascertainable by one skilled in the art. These elevation data and the projected pattern virtual point coordinates are combined to create the contour map 450.

Figure 10:
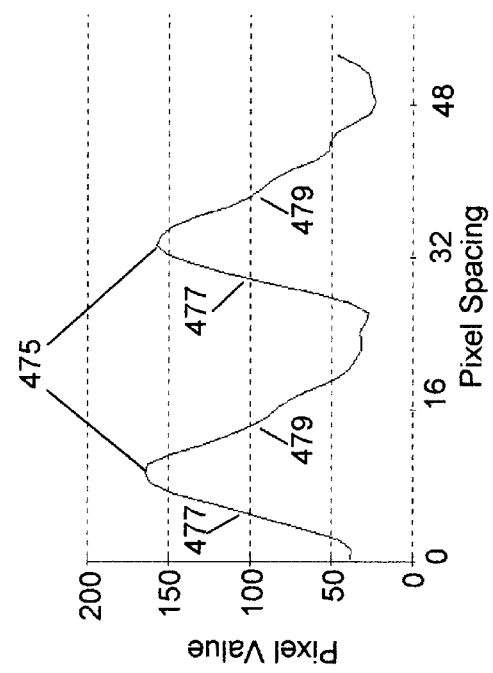
FIG. 10 is a graphical representation of a horizontal intensity profile of a portion of a pattern image of the present invention obtained from a fluorescent artificial cornea made from fluorescent plastic.

The advantage of using the contralateral edges within the pattern image to find the front surface for this fluorescing artificial cornea having a translucent substrate is shown in FIG. 10. FIG. 10 is a representative horizontal intensity profile through two horizontally adjacent quadrilaterals obtained from a pattern image acquired with imaging branch 61 along optical axis 63. The light quadrilaterals form intensity peaks 475 that have asymmetrical sides. The contralateral sides 477 have steep slopes that are formed by the contralateral edges. The ipsilateral sides 479 have lesser slopes due to the presence of the smearing effect produced in the pattern image by the secondary light region formed by light arising from beneath the front surface. The slopes of the ipsilateral edges vary with the fluorescence of the substrate and thus provide a less reliable reference feature by which to map the front surface. On the other hand, the contralateral edges provide a stable reference feature for the front surface. The upper portion of the ipsilateral sides 479 correspond to the boundary between the primary and secondary light regions, and the lower portion of the ipsilateral sides 479 correspond to the back surface ipsilateral edge.

In practicing the present invention, the peak 475 of a quadrilateral is not used as a reference feature. The peak 475 is not used because of the skew of the intensity profile, and also due to the fact that the location of the peak is determined in part by the degree of substrate translucency or fluorescence, which is not constant between patients and is not likely to be well controlled clinically. Thus, using the peaks of the quadrilaterals as a reference feature may lead to erroneous topographic information.

In practicing the present invention a fully calibrated instrument would be provided to an eye care practitioner. As part of the calibration process, the instrument has stored in it for use by the computer's algorithms the coordinates of the virtual points in the projected pattern, the path of the projected virtual point chief rays, functions for converting the image pattern's virtual points' coordinates to elevation data, and functions for converting the image pattern's virtual points' coordinates to image virtual point chief ray paths. The eye care practitioner would place the patient in the appropriate position relative to the apparatus by, for example, viewing the pattern image in live video during the alignment procedure. Upon alignment, at least one pattern image would be acquired by the frame grabber and transferred to the computer for analysis. The way in which the pattern image is analyzed depends on the surface(s) the practitioner desires to map and whether the patient's cornea is characterized as a thin film or translucent substrate.

Let it be assumed that it is desired to ascertain the topography of the front surface of the cornea as well as the thickness of the cornea of a patient who is undergoing a refractive surgery procedure wherein the epithelium is removed and the corneal stroma can be characterized as translucent at the time of measurement with the apparatus and method of the present invention. Firstly, the contralateral non-horizontal edges within at least one image pattern are used to determine, in conjunction with the horizontal features within the pattern image, the coordinates of the contralateral virtual points. These contralateral virtual point coordinates are used to determine the elevation of the front surface at the location on the front surface at which each of the contralateral virtual points is located within the projected pattern of the array of edges. A plurality of such points is used to provide a topographic map of the front surface using data interpolation and visualization methods known to those skilled in the art.

The practitioner then uses the front surface topographic map obtained to plan or modify the surgical procedure according to the measured topography of the cornea and the desired surgical outcome. The back surface ipsilateral non-horizontal edges are used in conjunction with the horizontal features within the pattern image, to determine the coordinates of the back surface ipsilateral virtual points. These back surface virtual point coordinates are used to determine the apparent elevation of the back surface, and, thus, the image path of the ipsilateral virtual points' chief rays. Using ray tracing methods hereinafter described, corrections then are made for refraction at the front surface and the actual back surface topography is reconstructed from the apparent back surface topography. The back surface topography is subtracted from the front surface topography to arrive at the corneal thickness map. The thickness map, in conjunction with the front surface topographic map and back surface topographic map, is used by the practitioner to plan or modify the surgical procedure to achieve the desired surgical outcome.

Thus it can be seen in connection with the present invention, that the unique properties of the contralateral edges are used to accurately find the front surface of objects which are characterized by a thick film and/or translucent substrate; and, the unique properties of the back surface ipsilateral non-horizontal edges are used to accurately find the back surface of thick films or objects which are characterized by a translucent substrate.

Figure 11:
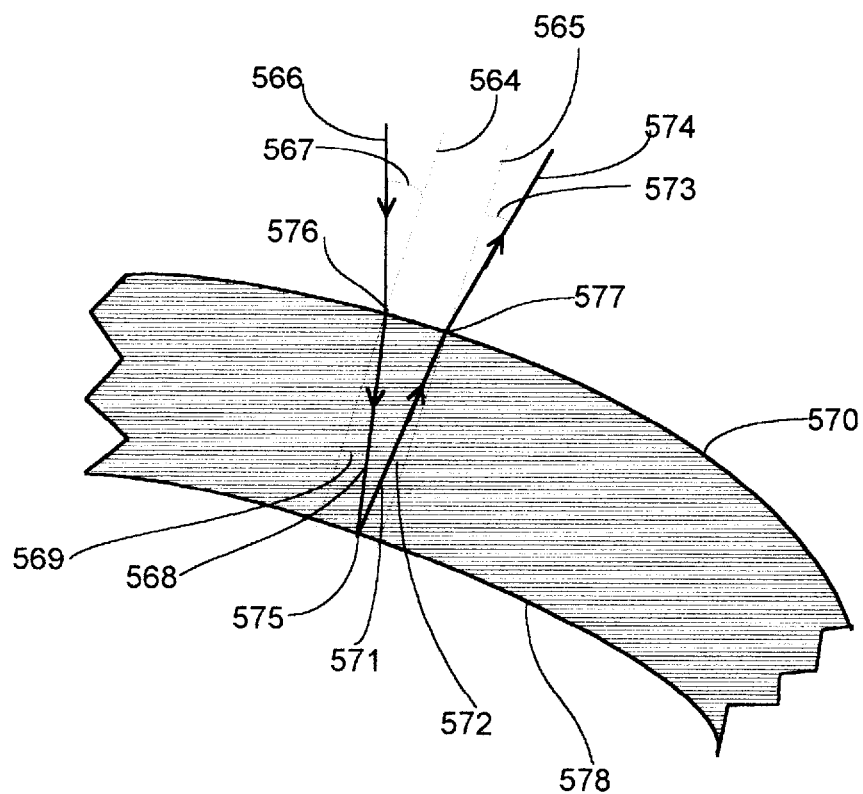
FIG. 11 is a cross sectional view of a cornea with ray traces showing the effect of refraction on the back surface coordinates of an ipsilateral virtual point in the x coordinate plane utilizing the apparatus shown in FIG. 1.

To map the back surface topography of a thick film or translucent substrate, the apparent back surface topography, as represented in the imaged back surface ipsilateral virtual points, needs to be corrected for refraction at the front surface. This is shown diagrammatically in FIG. 11 for a horizontal cross section through an object as for example a human cornea. The correction is made using ray tracing, just as if a virtual point were a real point formed by a bundle of light having a chief ray. Utilizing ray tracing methods are known to those skilled in the art and described in many text books, e.g. Jenkins, F. A. and White, H. E., *Fundamentals of Optics, Third Edition,* published in 1957 by McGraw-Hill Book Company in New York, Toronto, and London.

At the front surface boundary 570, the incident projected ipsilateral virtual point chief ray 566, forms an angle 567 to the normal 564. The normal is calculated from the local front surface topography as mapped with at least three contralateral virtual points using methods of interpolation and surface modeling known to those skilled in the art. An advantage to using a two imaging branch system, arranged as shown in FIG. 1, is that the elevation at the point of incidence 576 of the projected ipsilateral virtual point chief ray can be directly measured by the complementary contralateral virtual point of the complementary imaging branch. This obviates the need to interpolate the coordinates of the surface at this point. The refracted incident chief ray 568 makes an angle 569 to the normal that can be calculated using Snell's Law with the index of refraction of the object obtained from known sources, which for the cornea is about 1.336. Accordingly, the path of the refracted projected ipsilateral virtual point chief ray 568 within the cornea's stroma is known.

Similarly, the emerging imaged back surface ipsilateral virtual point chief ray 571 makes an angle 572 with a normal 565 to the front surface at point 577 and an angle 573 after refraction at the front surface thereby resulting in the imaged back surface ipsilateral virtual point chief ray 574. The path of the imaged back surface ipsilateral virtual point chief ray 574 can be ascertained from the pattern image coordinates of the back surface ipsilateral virtual point and the imaging branch's optical parameters. By reversal of the light path of the back surface ipsilateral virtual point chief ray, the path of the back surface ipsilateral virtual point chief ray within the stroma 571 can be calculated.

The coordinates of the ipsilateral virtual point, 575, on the back surface, 578, of the object, are found by solving for the intersection of the projected and imaged virtual point chief rays.

The thickness of a translucent substrate is found by subtracting the topographic map of the back surface from the topographic map of the front surface. Methods of interpolation known to those skilled in the art are used to find the elevation at corresponding sampling points along the front and back surfaces.

When there are two imaging branches positioned on opposite sides of the projection branch, as shown in FIG. 1, two pattern images are available for analysis and there are complementary pairs of imaged virtual points for each projected virtual point. This doubling of the contralateral and ipsilateral virtual points is a fundamental advantage of the present invention gained by utilizing two imaging branches disposed on opposite sides of the projection branch. Moreover, this apparatus configuration provides a corresponding contralateral image virtual point for each ipsilateral image virtual point, which is preferred when finding the back surface topography of translucent substrate objects, as hereinafter described.

There are additional advantages of two imaging branches disposed on opposite sides of the projection branch because each branch provides a separate pattern image for analysis. For thin films there is redundant data at each virtual point which can be averaged to improve accuracy and reduce noise in the data. The angle between the projection branch and an imaging branch can be larger than practically feasible, due to surface curvature, with a single imaging branch thus increasing the elevation resolution obtainable with the present apparatus. The apertures of each of the imaging branches can be increased to improve the signal to noise level of the video image; because, the region measured by each imaging branch can be smaller with a concomitant reduction in the elevation change that needs to be accommodated by the imaging branch's depth of field.

In regard to designing an array of edges, the width of the contiguous secondary light region, e.g. 308, 310 (FIG. 8A), 408, and 410 (FIG. 8B), in the image pattern created by translucent substrates determines the optimal horizontal spacing of the light regions within the projected light pattern. The ipsilateral and contralateral edges of horizontally neighboring light regions in projected light patterns must be sufficiently separated such that the position of the back surface ipsilateral edge does not overlay the contralateral edge of the adjacent primary light region in the pattern image. Thus, the spacing needs to be optimized for the angle between the projection and imaging branches, the thickness of a translucent substrate or thick film, and the desired sampling density along the surface. For a given translucent substrate or thick film, the required spacing within the projected pattern increases with the angle between the projection branch and the imaging branch.

Figure 12:
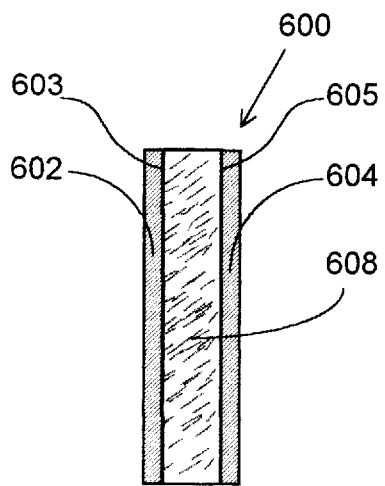
FIG. 12 is a side elevation view of a laminated reticule incorporating a structured light pattern of the present invention.

A thick reticule for use with the apparatus shown in FIG. 1 is shown in FIG. 12. The reticule 600 therein shown is comprised of an optical flat, 608, that may be fabricated from any appropriate material such as glass or plastic and is provided with spaced apart planar parallel surfaces 603 and 605 that are coated with an opaque material 604 and 602 such as a silver-chrome coating that can be etched. The coatings 604 and 602 carry identical patterns which may be of the type hereinbefore described. In use of the reticule 600, the projection branch 22 provides a fixed magnification for the reticule 600 positioned between the first focal plane and the first principal plane of lens 43 and therefore identical twin images will be formed in the corresponding conjugate planes at the object 29. Since the light impinging on the reticule is essentially collimated, little light is lost. Multiples of such reticules, or the equivalents, can be stacked together to extend the depth of field. Alternative fabrication methods, such as etching holes through a solid opaque material may be utilized to achieve the same result.

Figure 13:
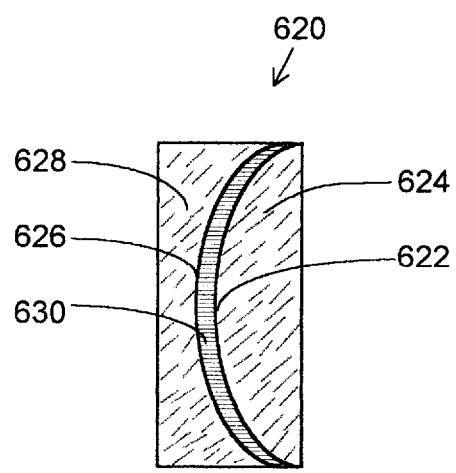
FIG. 13 is a cross sectional view of a curved reticule incorporating a structured light pattern of the present invention.

Another embodiment for a reticule that increases the efficiency of the apparatus when it is desirable to have a depth of field that is less than the elevation change over the region of the object being measured is shown in the curved reticule 620 in FIG. 13. The curved reticule 620 is comprised of first and second transparent rigid members or lens elements 624 and 628 having matching complementary first and second curved surfaces 622 and 626. Thus, lens element 624 is a plano convex lens and lens element 628 is a plano concave lens. Both lenses are formed of material with the same index of refraction. Pattern carrying means in the form of an etched metallic coating 630 can be provided on either of the surfaces 622 or 626 thereby being disposed between the transparent first and second rigid members and sandwiched between curved surfaces 622 and 626. Means such as a transparent adhesive (not shown) deposited between the surfaces 622 and 626 is provided for fastening the first and second members with the pattern carried thereby into a unitary assembly as shown in FIG. 13. The curved surfaces 622 and 626 of the first and second transparent rigid members have curvatures corresponding generally to the curvature of the object whereby when the curved reticule is used in the projection branch 22 a projected pattern is provided which is in focus over the surface of the object.

Intraoperatively the cornea often looses transparency and becomes more diffuse, thus reducing the need to use fluorescein to simulate a diffusing surface. However, when fluorescein is not used the image pattern of the projected structured light pattern is obtained not only from the cornea, but also from more posterior structures including the iris and lens of the eye. Because a short depth of field can be selectively distributed over the surface of interest by using curved reticule 620, the structured light pattern can be made to be in focus at the cornea, but blurred at the iris and lens, thereby reducing the prevalence within the image pattern of the competing structured light pattern which arises from the inner ocular structures such as the iris and the lens.

For ophthalmic object imaging, blur may occur across the field of the pattern image due to portions of the object 29, which typically is curved, lying outside the depth of field of the projection branch and/or imaging branch(es). Thus it may be desirable to incorporate calibration methods, known to those skilled in the art, that account for any influence of blur on the location of the structured light features in the projected pattern and image pattern.

The projection branch calibration, using techniques known to those skilled in the art, is complete when the X and Y coordinates of the array of virtual points, as projected onto the object, are known. These coordinates are used to specify the position on the surface being measured and the point of incidence of a projected virtual point's chief ray.

An imaging branch is calibrated when the pattern image coordinates of a virtual point can be computed to a corresponding surface elevation. A preferred method for achieving this, when a back surface of a thick film or translucent substrate is to be mapped, is to model the optical properties of the imaging branch and the geometric relationships between the projection and imaging branches such that a chief ray triangulation can be performed as described in U.S. Pat. No. 4,761,071. Alternatively, for front surface mapping, a simplified calibration method treats the entire system as a black box that simply correlates the coordinates of an image virtual point with a particular elevation.

Thus, it can be seen that use of an edge array, as performed by the present invention, provides unique topographic mapping properties. The contralateral edges and associated contralateral virtual points maintain their position and elevation measuring accuracy over a broad range of object substrate optical parameters, thereby providing the eye care practitioner a reliable and accurate means of mapping the cornea's shape for a broad spectrum of eye diseases and conditions. The ipsilateral edges and associated ipsilateral virtual points provide a means of mapping the back surface of an object with a translucent substrate. By subtracting the front and back surface topographies, the thickness of the object can be mapped across the full extent of the cornea and correlated with its front and back surface topographies.

What is claimed:

1. Apparatus for determining the topography of a surface of an object comprising projection branch means for projecting along a first optical axis a predetermined projected structured light pattern onto the surface of the object, said predetermined projected structured light pattern having light and dark regions that form an array comprised of horizontal features and non-horizontal edges and a plurality of projected virtual points with each of the projected virtual points being defined by the intersection of first and second functions wherein the first function is defined by a first non-horizontal edge and the second function is selected from a function defined by a second non-horizontal edge and a function defined by a horizontal feature, image branch detecting means for detecting an image pattern of the predetermined projected structured light pattern on the surface of the object along a second optical axis angled with respect to the first optical axis of the projection branch means, computer means coupled to the image branch detecting means for establishing the coordinates of a plurality of image virtual points in the image pattern by finding for each image virtual point the intersection of first and second functions wherein the first function is fitted to a first non-horizontal edge and the second function is selected from a function fitted to a second non-horizontal edge and a function fitted to a horizontal feature, means for determining an elevation at each of a plurality of locations on the surface of the object from the coordinates of the plurality of image virtual points for ascertaining the topography of at least a portion of the surface of the object.

2. Apparatus as in claim 1 wherein the predetermined projected structured light pattern is in the form of quadrilaterals in a predetermined pattern, each quadrilateral having a vertical dimension and a horizontal dimension.

3. Apparatus as in claim 2 wherein at least certain of the quadrilaterals are vertically disposed and wherein at least two of the quadrilaterals are juxtaposed to form a pair of quadrilaterals.

4. Apparatus as in claim 3 wherein the horizontal feature is a straight line function derived from a pair of horizontal edges and is spaced between the horizontal edges.

5. Apparatus as in claim 3 wherein the pair of quadrilaterals has non-horizontal edges that are paired to define the first and second functions which intersect to provide a virtual point.

6. Apparatus as in claim 3 a wherein the pair of quadrilaterals has paired non-horizontal edges to define a continuous function as the first function that intersects with the second function which is defined by a horizontal feature to define a virtual point.

7. Apparatus as in claim 2 wherein each of the quadrilaterals has a first non-horizontal edge to provide the first function and a horizontal edge providing a horizontal feature to provide the second function of the projected structured light pattern.

8. Apparatus as in claim 2 wherein each of the quadrilaterals has a vertical dimension which is substantially less than the horizontal dimension.

9. Apparatus as in claim 1 further including a second image branch detecting means for providing a second pattern image of the projected structured light pattern along a third optical axis angled with respect to the first and second optical axes so that first and second pattern images of the projected structured light pattern are provided simultaneously.

10. Apparatus as in claim 1 wherein the object carries a fluorescing agent, said projected structured light pattern exciting the fluorescing agent to provide an emission of fluorescent light and wherein said image branch detecting means for providing a pattern image of the projected structured light pattern includes means for detecting the fluorescent light.

11. Apparatus as in claim 10 wherein the projection branch means includes a fluorescent excitation filter and wherein the image branch detecting means includes a fluorescent emission filter.

12. Apparatus as in claim 1 wherein said projection branch means includes optics for projecting a substantially collimated light pattern onto the object.

13. Apparatus as in claim 1 wherein the projection branch means includes a thick reticle.

14. Apparatus as in claim 1 wherein the projection branch means includes a curved reticle.

15. A method for determining the topography of a surface of an object comprising projecting a predetermined projected structured light pattern along a first optical axis onto the surface of the object to provide a predetermined projected light pattern having light and dark regions forming an array comprised of non-horizontal edges and horizontal features and a plurality of projected virtual points with each of the projected virtual points being defined by the intersection of first and second functions wherein the first function is defined by a first non-horizontal edge and the second function is selected from a function defined by a second non-horizontal edge and a function defined by a horizontal feature, detecting an image pattern of the predetermined projected light pattern along a second optical axis angled with respect to the first optical axis of the predetermined projected structured light pattern, the image pattern having light and dark regions forming an array comprised of non-horizontal edges and horizontal features, establishing the coordinates of a plurality of image virtual points in the image pattern by finding for each virtual point the intersection of first and second functions wherein the first function is fitted to a first non-horizontal edge and the second function is selected from a function fitted to a second non-horizontal edge and a function fitted to a horizontal feature, determining an elevation at each of a plurality of locations on the surface of the object from the coordinates of the image virtual points to ascertain the topography of at least a portion of the surface of the object.

16. A method as in claim 15 further comprising establishing the coordinates of a virtual point in the predetermined projected light pattern by the intersection of a first function defined by a first non-horizontal edge and a second function defined by a second non-horizontal edge.

17. A method as in claim 15 further comprising forming the predetermined pattern of the projected structured light pattern into quadrilaterals in which at least certain of the quadrilaterals are vertically disposed and at least two quadrilaterals are juxtaposed to form a pair having paired non-horizontal edges.

18. A method as in claim 17 further comprising determining the coordinates of a projected virtual point by the intersection of the first and second functions which are used to model the paired non-horizontal edges.

19. A method as in claim 17 further comprising defining the coordinates of a projected virtual point by finding the intersection of a first function defined by at least one non-horizontal edge and a second function defined by a horizontal feature.

20. A method as in claim 19 further comprising using as the horizontal feature a straight line function derived from a pair of horizontal edges and spaced between the horizontal edges.

21. A method as in claim 19 further comprising defining the coordinates of a projected virtual point by the intersection of a first function defined by paired non-horizontal edges of the pair of quadrilaterals and a second function defined by a horizontal feature.

22. A method as in claim 15 further comprising forming the predetermined pattern of the projected structured light pattern into thin quadrilaterals having first and second horizontal ends defining the coordinates of a projected virtual point by the intersection of the first function defined by a non-horizontal edge and the second function defined by a horizontal line corresponding to the midline of a thin quadrilateral having first and second horizontal ends.

23. A method as in claim 15 wherein the object has a translucent substrate and in which the image pattern includes an array of non-horizontal contralateral edges, the method further comprising for each front surface image virtual point, fitting the first function to a non-horizontal contralateral edge to avoid the effects on the image pattern of light arising from within the substrate.

24. A method as in claim 15 wherein the object has front and back surfaces and the image pattern has back surface ipsilateral non-horizontal edges, the method further comprising using the image virtual points derived from the back surface ipsilateral non-horizontal edges to distinguish the apparent back surface from the front surface.

25. A method according to claim 15 further including the steps of determining the coordinates of an image virtual point using more than one pair of functions to find redundant intersection coordinates to thereby test the accuracy of the coordinates of the image virtual point determined by any one pair of intersecting functions.

26. A method according to claim 15, using chief ray triangulation to convert the image virtual point coordinates into three dimensional elevation coordinates.

27. A method according to claim 15, further comprising performing chief ray triangulation using the geometric relationships between the first optical axis and second optical axis to convert from image virtual point coordinates to elevation coordinates.

28. A method according to claim 15, further comprising applying a fluorescent substance to the object so that it fluoresces and imaging essentially only the fluorescent light emitted by the fluorescing object.

29. A method as in claim 15 wherein the object has front and back surfaces and in which the image pattern is comprised of an array of edges having non-horizontal front surface contralateral edges and non-horizontal back surface ipsilateral edges with associated front surface contralateral virtual points and associated back surface ipsilateral virtual points, the method further comprising ascertaining the topography of the back surface by the steps of using the front surface contralateral virtual points to determine the topography of the front surface, using the front surface topography to find the angle of incidence of the chief ray of a projected ipsilateral virtual point to calculate the path of the chief ray of the projected ipsilateral virtual point within the substrate of the object, using the contralateral virtual points to determine the front surface topography to find the angle of incidence of the chief ray of an image back surface ipsilateral virtual point and using the paths of the projected and imaged back surface ipsilateral image virtual point chief rays to calculate the back surface coordinates of the point of intersection of the projected and imaged chief rays.

30. A method according to claim 15 wherein the object has front and back surfaces and in which the image pattern is comprised of an array of edges having non-horizontal front surface contralateral edges and non-horizontal back surface ipsilateral edges with associated front surface contralateral image virtual points and associated back surface ipsilateral image virtual points, the method further comprising mapping the topography of the back surface by the steps of using the contralateral image virtual points to find the front surface topography and utilizing ray tracing with the information provided by the ipsilateral and contralateral image virtual points to establish the topography of the back surface.

31. A method as in claim 30 further comprising utilizing the difference between the front and back surface topography maps to ascertain the thickness of the object.

* * * * *

UNITED STATES PATENT AND TRADEMARK OFFICE
CERTIFICATE OF CORRECTION

PATENT NO. : 5,867,250  Page 1 of 2
DATED : February 2, 1999
INVENTOR(S) : Baron It is certified that error appears in the above-identified patent and that said Letters Patent is hereby corrected as shown below:

On the title page, item [57], after "ABSTRACT" delete the next paragraph in its entirety and substitute the following paragraph:

--Apparatus for determining the topography of a surface of an object comprising a projection branch for projecting along a first optical axis a predetermined projected structured light pattern onto the surface of the object. The predetermined projected structured light pattern has light and dark regions that form an array comprised of horizontal features and non-horizontal edges and a plurality of projected virtual points with each of the projected virtual points being defined by the intersection of first and second functions. The first function is defined by a first non-horizontal edge and the second function is selected from a function defined by either a horizontal feature or a second non-horizontal edge. An imaging branch detecting means, which is connected to a computer, provides a pattern image of the predetermined projected structured light pattern on the surface of the object along a second optical axis angled with respect to the first optical axis of the projection branch. A computer algorithm establishes the coordinates for each of a plurality of image virtual points within the image pattern by finding for each image virtual point the intersection of first and second functions. The first function is fit to a first non-horizontal edge and the second function is selected from a function that is fit either to a horizontal feature or to a second non-horizontal edge. The computer algorithm determines

UNITED STATES PATENT AND TRADEMARK OFFICE
CERTIFICATE OF CORRECTION

PATENT NO. : 5,867,250
DATED : February 2, 1999
INVENTOR(S) : Baron

It is certified that error appears in the above-identified patent and that said Letters Patent is hereby corrected as shown below:

an elevation at each of a plurality of locations on the surface of the object from the coordinates of the plurality of image virtual points to ascertain the topography of at least a portion of the surface of the object.--

Signed and Sealed this

Twentieth Day of July, 1999

*Attest:*

Q. TODD DICKINSON

*Attesting Officer*   *Acting Commissioner of Patents and Trademarks*